US005672361A

United States Patent [19]
Halberstadt et al.

[11] Patent Number: 5,672,361
[45] Date of Patent: Sep. 30, 1997

[54] LAMININ 5 FOR GROWTH OF PANCREATIC ISLET CELLS

[75] Inventors: Craig Halberstadt, San Diego; John J. Grzesiak, Cardiff, both of Calif.

[73] Assignee: Desmos, Inc., San Diego, Calif.

[21] Appl. No.: 626,242

[22] Filed: Mar. 29, 1996

[51] Int. Cl.$^6$ .......................... A61K 35/39; A61K 38/28; C12N 5/06; C12N 5/08
[52] U.S. Cl. .......................... 424/556; 424/93.7; 424/562; 435/350; 435/351; 435/352; 435/363; 435/366; 435/402; 514/3
[58] Field of Search .................................. 424/93.7, 520, 424/550, 562, 572, 556; 435/240.2, 240.21, 240.23, 402, 366, 350, 351, 352, 363; 514/3

[56] References Cited

U.S. PATENT DOCUMENTS 5,422,264  6/1995  Quaranta et al. .
5,510,263  4/1996  Quaranta et al. .

FOREIGN PATENT DOCUMENTS

WO 92/17498  10/1992  WIPO .
WO 94/05316  3/1994   WIPO .
WO 94/23016  10/1994  WIPO .
WO 95/06660  3/1995   WIPO .
WO 95/29988  11/1995  WIPO .

OTHER PUBLICATIONS

W.G. Carter, et al. (1991) "Epiligrin, a New Cell Adhesion Ligand For Integrin α3 β1 IN Epithelial Basement Membranes", *Cell*, 65:599–610.

Y. Hieda et al. (1992) "Identification of a New Hemidesmosomal Protein, HD1: A Major, High Molecular Mass Component of Isolated Hemidesmosomes", *The Journal of Cell Biology*, 116(6):1497–1506.

B. Hsi, et al. (1987) "Monoclonal Antibody GB$_3$6 Raised Against Human Trophoblast Recognizes a Novel Epithelial Antigen", *Placenta*, 8:209–217.

H. Iwata, et al. (1994) "Feasibility of Agarose Microbeads With Xenogeneic Islets as a Bioartificial Pancreas", *Journal of Biomedical Materials Research*, 28:1003–1011.

K. Izumi, et al. (1981) "In Vitro Induction of Ornithine Decarboxylase in Urinary Bladder Carcinoma Cells", *Cancer Research*, 41:405–409.

K. Kover et al. (1989) "Development of a Method For Isolation of Islets from Human Fetal Pancreas", *Diabetes*, 38:917–924.

M. Langhofer, et al. (1993) "The Matrix Secreted By 804G Cells Contains Laminin–Related Components That Participate in Hemidesmosome Assembly in Vitro", *Journal of Cell Science*, 105:753–764.

R.P. Lanza, et al. (1993) "Biohybrid Artificial Pancreas", *Transplantation*, 56(5):1067–1072.

F.N. Leach, et al. (1973) "Insulin Release From Human Foetal Pancreas in Tissue Culture", *J. Endocr.*, 59:65–79.

T. Otonkoski, et al. (1988) "Morphology, Yield and Functional Integrity of Islet–Like Cell Clusters in Tissue Culture of Human Fetal Pancreata Obtained After Different Means of Abortion", *Acta Endocrinologica*, 118:68–76.

K.S. Riddelle, et al. (1991) "Formation of Hemidesmosomes in Vitro by a Transformed Rat Bladder Cell Line", *The Journal of Cell Biology*, 112(1):159–168.

K.S. Riddelle, et al. (1992) "Hemidesmosomes in the Epithelial Cell Line 804G: Their Fate During Wound Closure, Mitosis and Drug Induced Reorganization of the Cytoskeleton", *Journal of Cell Science*, 103:475–490.

P. Rousselle, et al. (1991) "Kalinin: An Epithelium–Specific Basement Membrane Adhesion Molecule That is a Component of Anchoring Filaments", *The Journal of Cell Biology*, 114(3):567–576.

P. Rousselle, et al. (1994) "Kalinin is More Efficient Than Laminin in Promoting Adhesion of Primary Keratinocytes and Some Other Epithelial Cells and Has a Different Requirement For Integrin Receptors", *The Journal of Cell Biology*, 125(1):205–214.

S. Sandler, et al. (1985) "Tissue Culture of Human Fetal Pancreas", *Diabetes*, 34:1113–1119.

A.M. Simpson, et al. (1991) "Characterization of Endocrine–Rich Monolayers of Human Fetal Pancreas That Display Reduced Immunogenicity", *Diabetes*, 40:800–808.

H.D. Soule, et al. (1990) "Isolation and Characterization of a Spontaneously Immortalized Human Breast Epithelial Cell Line, MCF–10", *Cancer Research*, 50:6075–6086.

L.A. Staehelin (1974) "Structure and Function of Intercellular Junctions", *Department of Molecular, Cellular and Development Biology, University of Colorado, Boulder, Colorado*, pp. 191–283.

L. Tait, et al. (1990) "Ultrastructural and Immunocytochemical Characterization of an Immortalized Human Breast Epithelial Cell Line, MCF–10", *Cancer Research*, 50:6087–6094.

P. Verrando, et al. (1987) "Monoclonal Antibody GB3, A New Probe For The Study of Human Basement Membranes and Hemidesmosomes", *Experimental Cell Research*, 170:116–128.

P. Verrando, et al. (1988) "The New Basement Membrane Antigen Recognized by the Monoclonal Antibody GB3 is a Large Size Glycoprotein: Modulation of its Expression by Retinoic Acid", *Biochimica et Biophysica Acta*, 942:45–56.

F. Voss, et al. (1989) "Transplantation of Proliferated Human Pre–Islet Cells Into Diabetic Patients With Renal Transplants", *Transplantation Proceedings*, 21(1):2751–2756.

Maes, E. and Pipeleers, D. Endocrinology. 114(6): 2205–2209 Jun. 1994.

Dahl, G. and Gratzl, M. Cytobiologie. 12(2): 344–355 Feb. 1976.

Primary Examiner—Christina Chan
Assistant Examiner—F. Pierre VanderVegt
Attorney, Agent, or Firm—Knobbe, Martens, Olson & Bear

[57] ABSTRACT

A method of expanding the number of pancreatic islet cells for transplantation. Fetal islet cells are cultured in the presence of laminin 5 extracellular matrix, resulting in a significant increase in cell number after passaging in culture. The expanded islet cells contain insulin and respond to glucose challenge.

13 Claims, No Drawings

LAMININ 5 FOR GROWTH OF PANCREATIC ISLET CELLS

FIELD OF THE INVENTION

The present invention relates to the enhanced growth of pancreatic islet cells by contacting the cells with a laminin 5 soluble or insoluble extracellular matrix.

BACKGROUND OF THE INVENTION

When organs of the body are formed, they develop in neatly organized arrays. Often, cell types are separated by connective tissue called basement membranes. In skin, for instance, the superficial layer of epidermal cells adheres to the underlying basement membrane. This skin basement membrane acts as a barrier between the epidermal cells on the outside, and the dermal cells underneath. A similar arrangement of cells occurs in the lining of the gut and in the oral cavity.

Basement membranes have been implicated in the growth, attachment, migration, repair and differentiation of their overlying cell populations. Three layers have been defined in basement membranes: a) the lamina lucida, an electronmicroscopically clear region in close approximation to the overlying cells; b) the lamina densa, an electron dense region of 20–300 nm in width; and c) the sublamina densa which contains anchoring fibrils, microfibrillar bundles and collagen fibers.

Many different types of compounds have now been localized to the basement membrane. Some of these compounds are laminin, collagen IV and heparin sulfate proteoglycans (Verrando et al., *Exp. Cell Res.*, 170:116–128, 1987). In addition, specific basement membranes include other biologically active compounds, such as nidogen and entactin.

One major cell adhesion receptor which epidermal cells use to attach to the basement membrane is called $\alpha_6\beta_4$. This transmembrane receptor is formed by a combination of two protein moieties $\alpha_6$ and $\beta_4$ which are derived from different genes. These genes are members of the integrin cell adhesion receptor superfamily.

Many epithelial cells interact with the underlying extracellular matrix, a network of proteins to which cells attach, via a junction called the hemidesmosome (Staehelin, (1974) *Structure and Function of Intercellular Junctions*, Department of Molecular, Cellular and Developmental Biology, University of Colorado, Boulder, Colo., 191–283). The hemidesmosome, with its anchored structures including intermediate filaments and anchoring fibrils, forms an adhesion complex.

When cultured on tissue culture plastic in vitro, most epithelial cells do not assemble bona fide hemidesmosomes despite the fact that they appear to express all of the necessary plaque and hemidesmosomal components. The 804G and NBT-II rat bladder carcinoma cell lines are capable of assembling hemidesmosomes in vitro under standard culture conditions (Riddelle et al., (1991) *J. Cell Biol.*, 112:159–168; Hieda et al., (1992), *J. Cell Biol.*, 116:1497). It has also been reported that substratum-induced staining by anti-hemidesmosome antibodies is greatly diminished in 804G cell cultures that enter in vitro wound sites (Riddelle et al., (1992) *J. Cell Sci.*, 103:475–490).

As described in Langhofer et al. (1993) *J. Cell Sci.*, 105:753–764) and in U.S. Pat. No. 5,541,106, the entire contents of which are hereby incorporated by reference, when epithelial cells unable to themselves form hemidesmosomes are plated on the cell matrix deposited by 804G rat bladder carcinoma cells, hemidesmosome formation is induced.

In addition, U.S. Pat. No. 5,422,264, the entire contents of which are hereby incorporated by reference, discloses that a soluble matrix equivalent produced by 804G cells can also induce attachment and hemidesmosome formation in cells contacted with the soluble matrix. The 804G matrix and soluble matrix equivalent contain the same major protein components. These proteins exhibit significant similarity to human merosin, a laminin A isoform, and to *Drosophila laminin* A.

U.S. Pat. No. 5,510,263, the entire contents of which are hereby incorporated by reference, discloses the enhanced growth of pancreatic islet cells cultured on the 804G and NBT-II extracellular matrices.

Human cell matrix molecules structurally similar, if not identical, to the 804G matrix have also been described. Rouselle et al. (*J. Cell Biol.*, 114:567–576, 1991) and Burgeson et al. (PCT WO92/17498; PCT WO94/05316) describe a molecule called kalinin which is secreted into the culture medium by human keratinocytes and enhances cell attachment. Carter et al. (*Cell*, 65:599–610, 1991; PCT WO95/06660) describe an epithelial ligand complex called epiligrin found in the extracellular matrix of human keratinocytes. In addition, a basement membrane glycoprotein secreted into the culture medium of human keratinocytes (BM600) (Verrando et al., *Biochem. Biophys. Acta.*, 942:45–56, 1988; Hsi et al., *Placenta* 8:209–217, 1987) is structurally similar to 804G matrix. Although kalinin and epiligrin stimulate adhesion of cells to a substrate, they have not been reported to induce formation of hemidesmosomes or to stimulate growth of pancreatic islet cells.

Nearly two million Americans are afflicted with Type I (insulin-dependent) diabetes, in which the pancreas has lost its ability to secrete insulin due to an autoimmune disorder in which the insulin-secreting beta cells, found within the islet cells of the pancreas, are destroyed. Although insulin injections can compensate for beta cell destruction, blood sugar levels can still fluctuate dramatically. The impaired ability to take up glucose from the blood results in side reactions in which toxic products accumulate, leading to complications including blindness, kidney disease, nerve damage, and, ultimately, coma and death.

Researchers have tried smaller, more frequent doses of insulin and mechanical pumps which mimic the action of the pancreas, but the results have been far from ideal. Another option, pancreatic transplant, requires major surgery and is accompanied by many complications. In addition, the limited number of donor pancreases leaves a significant number of diabetics without hope for transplantation.

The most promising option thus far is islet cell transplantation using tissue derived from either cadavers or human fetuses. This procedure has had moderate success. Among the transplants from cadavers performed worldwide, the transplanted tissue survived for a full year in about 20% of recipients. Ten of these recipients are now insulin-independent, while others have a greatly reduced need for insulin. The main problems associated with islet cell transplantation include rejection by the immune system and the autoimmune disorder which caused the disease in the first place which, if left unchecked, will also destroy the transplanted islet cells. In addition, the expansion of adult pancreatic islet cells in culture has not been attained.

Fetal pancreatic tissue has also been used as a source of islet cells (Voss et al., *Transplantation Proc.*, 21:

2751–2756, 1989). Earlier attempts at culturing pancreatic islet cells were complicated by fibroblast contamination (Leach et al., *J. Endocrinol.*, 59: 65–79, 1973). Although partially digested fetal pancreas has been used to produce pancreatic islet-like cell clusters (ICCs), the clinical use of these clusters is limited because only 100–200 can be obtained per pancreas (Sandler et al., *Diabetes*, 34: 1113–1119, 1985; Otonkoski et al., *Acta. Endocrinol.*, 118: 68–76, 1988). Kover and Moore (*Diabetes*, 38: 917–924, 1989) obtained 200–300 islets from a 17 week fetal pancreas, still not enough to be clinically useful. Finally, Simpson et al. (*Diabetes*, 40: 800–808, 1991) generated insulin-secreting, fibroblast-free monolayers of human fetal pancreas plated on bovine corneal matrix, although adequate numbers of cells for clinical transplantation could not be obtained. Although only a small number of cells within the clusters stained positively for the different pancreatic hormones, they differentiated efficiently into mature endocrine cells following transplantation into nude mice (Sandler et al., *Diabetes*, 34: 1113–1119, 1985).

Peck et al. (PCT W095/29988) disclose the culturing of pluripotent pancreatic stem cells in vitro. After several weeks, a stromal cell layer was formed. Islet cell differentiation was initiated by refeeding with high amino acid medium supplemented with homologous normal serum containing glucose. After an additional growth period, functional islet cells were recovered by standard techniques.

Thus, there is a need for a simple, reproducible, efficient method of expansion of the pool of available pancreatic islet cells for transplantation into diabetic patients. The present invention satisfies this need.

SUMMARY OF THE INVENTION

One embodiment of the present invention is a method of growing cells of pancreatic islet-like cell clusters (ICCs), comprising the step of culturing the ICCs in culture media in contact with laminin 5, with the proviso that the laminin 5 is not rat laminin 5. Preferably, the ICCs are from a mammal; most preferably, they are from a human. Advantageously, the laminin 5 is kalinin or epiligrin. In another aspect of this preferred embodiment, the laminin 5 is the extracellular matrix obtainable from MCF 10A cells. Advantageously, the laminin 5 is of human origin. Preferably, the ICCs are expanded at least 5 fold and the expanded ICCs secrete insulin.

The present invention also provides pancreatic ICCs prepared as described above.

Another embodiment of the invention is a method of treating Type I diabetes in a patient in need thereof, comprising the step of administering to the patient an effective insulin-producing amount of the pancreatic ICCs produced as described above. Preferably, the administering step is by implantation under the kidney capsule. Further, the ICCs may be placed in an immunoprotective barrier prior to implantation. Alternatively, the administering step is by direct injection into the liver. Preferably, the effective insulin-producing amount is between about $2\times10^5$ and about $8\times10^5$ ICCs.

DETAILED DESCRIPTION OF THE INVENTION

The present invention includes the discovery that certain cell lines produce an extracellular matrix that is capable of stimulating growth of adult pancreatic islet cells cultured thereon. One such cell line is the rat bladder carcinoma cell line 804G. This cell line is described by Izumi, et al., *Cancer Res.* (1981); 41:405–409, and is maintained as a Budapest Treaty patent deposit with the American Type Culture Collection (ATCC), Rockville, Md, under accession number ATCC 11555, made Feb. 24, 1994. Another such cell line is the rat bladder carcinoma cell line NBT-II which is maintained as a Budapest Treaty patent deposit with ATCC under accession number ATCC 11556 made Feb. 24, 1994. All restrictions upon availability to the public of these cell lines will be irrevocably removed upon issuance of a patent.

Human keratinocytes also secrete such extracellular matrix molecules, as does the human mammary epithelial cell line MCF 10A which is also available from ATCC (ATCC CRL 10317). This cell line is described by Soule et al. (*Cancer Res.*, 50:6075–6086, 1990) and Tait et al. (*Cancer Res*, 50:6087–6094, 1991).

It is also contemplated that other structurally and functionally similar laminin-like molecules will also enhance the growth of pancreatic islet cells cultured thereon. Such molecules are called "laminin 5" and include BM600, kalinin and epiligrin produced by human keratinocytes as well as the soluble/insoluble matrix produced by MCF 10A cells.

As described in U.S. Pat. No. 5,541,106, ultrastructural data have been developed demonstrating that the 804G matrix is capable of inducing a number of cells to develop mature hemidesmosomes and attach to their growth substrate. Further, it has been discovered that the 804G extracellular matrix contains laminin-like molecules that participate in hemidesmosome assembly. Three of these molecules have been cloned from a rat 804G cDNA library and encode proteins of 150, 140 and 135 kDa.

Thus, the matrix produced by such cells as 804G and NBT-II cells can modulate the organization of hemidesmosomal antigens in unrelated cells maintained upon it. This effect appears specific to hemidesmosomal elements since adhesion plaque components do not obviously change their localization in cells maintained upon the matrix.

The expansion of adult pancreatic islet cells either in vitro or in vivo has not been previously demonstrated. Although methods related to expansion of pancreatic islet cells by culturing on laminin 5 are specifically disclosed, it can be appreciated that any cell matrix having the ability to support pancreatic islet cell expansion thereon is within the scope of the present invention, regardless of its ability to stimulate hemidesmosome formation. Such laminin 5 matrices include kalinin, epiligrin, MCF 10A matrix and BM600. Because the extracellular matrix secreted by both 804G and NBT-II cells contains the same protein components as determined by immunoblotting experiments, the NBT-II matrix is also expected to support the expansion of mature pancreatic islet cells. However, only the 804G, NBT-II and MCF 10A matrix induce formation of hemidesmosomes in epithelial cells cultured thereon.

One preferred embodiment of the present invention is the growth of increase numbers of pancreatic islet-like cell clusters (ICCs). For example, fetal pancreatic ICCs may be grown in vitro in the presence of laminin 5 for transplantation into diabetic patients. The laminin 5 will increase the yield of fetal ICCs for transplantation and will thus solve the established need for greater numbers of these cells. Expansion of 5, 10, 50, 100, 500, 1000 or more times is possible with the present invention.

The resulting cell clusters will differentiate into functional pancreatic endocrine cells after transplantation into mammals, preferably humans, and will reduce or eliminate the need for insulin injections. It should be noted that the term "laminin 5" is used to generically refer to any of the 804G structurally-related cell matrix molecules capable of stimulating the growth of pancreatic islet cells and the term "adult pancreatic islet cells" refers to those fully differentiated pancreatic cells capable of secreting insulin. As defined herein, 804G matrix comprises one or more protein components deposited by 804G rat bladder carcinoma cells which facilitates growth of pancreatic islet cells. The term "804G soluble matrix" refers to the soluble matrix equivalent secreted by 804G cells into the culture medium. Structurally equivalent soluble matrices include kalinin and the soluble matrix secreted by MCF 10A cells.

A substrate upon which pancreatic islet cells are to be grown is coated with the matrix deposited by or soluble matrix secreted by 804G cells; with 804G conditioned medium, or with any of the other structurally and functionally similar molecules described herein. The 804G matrix is isolated as described in application Ser. No. 08/324,367. Purification of the soluble matrix from 804G conditioned medium is described in U.S. Pat. No. 5,422,264.

Kalinin and epiligrin are present in the conditioned medium of human keratinocytes. The conditioned medium itself may be used as a source of kalinin and epiligrin. Kalinin may be immunopurified from conditioned medium using an immunoaffinity column directed against its BM165 antigen (Rouselle et al., *J. Cell Biol.*, 125:205–214, 1994). Epiligrin is also present in the cell matrix secreted by human keratinocytes and may be isolated by a three-step extraction procedure comprising 1% w/v TRITON X-100® to solubilize membrane and cytoplasmic components; 2M urea and 1M NaCl to remove nuclear and cytoskeletal components; and 8M urea to solubilize residual components. 0.5% (w/v) sodium dodecyl sulfate (SDS) is then added and the matrix removed by scraping (Carter et al., *Cell*, 65:599–610, 1991; PCT W095/06660). MCF 10A matrix is isolated as described in Example 1. It will be appreciated that any soluble or insoluble cell matrix having the ability to support pancreatic ICC cell adhesion and expansion is within the scope of the present invention.

The cells to be grown are then plated on or applied to the matrix-coated substrate using standard tissue culture techniques, followed by expansion by passaging in standard cell growth medium. Any medium capable of supporting the enhanced growth of adult islet cells on the matrix-coated substrate is within the scope of the invention. Such cells, including human cells in vitro and in vivo, will grow in an organized fashion on the substrate and will exhibit significantly enhanced growth compared to pancreatic islet cells grown on conventional matrices such as bovine corneal matrix (BCM). It appears that the organization of islet cells growing on the 804G matrix is significantly more advanced and more tissue-like than cells grown in the absence of 804G matrix.

The islet cells can be removed from the original substrate and transferred to several new substrates coated with laminin 5, allowing large-scale expansion of these cells. The cells are tested for their ability to respond to a glucose challenge by measuring the levels of insulin secreted into the culture medium by well known methods. After culturing, the cells can be re-aggregated into three-dimensional structures and either placed into an immunoprotective barrier such as sodium alginate, hollow fibers or polyethylene glycol (Lonza et al., *Transplantation*, 56:1067–1072, 1993; Iwata et al., *J. Biomed. Materials Res.*, 28:1003–1011, 1994 or directly implanted in vivo for treatment of diabetes. The cells are also analyzed for insulin content by ELISA or radioimmunoassays known to one of ordinary skill in the art.

The substrate on which pancreatic islet cells are grown may be any desired substrate. For laboratory use, the substrate may be as simple as glass or plastic. Alternatively, any suitable substrate may be used, including various shaped articles, fabrics, prosthetic implants, and the like. For use in vivo, the substrate may be any biologically compatible material on which pancreatic islet cells can grow. Suitable substrate materials may include shaped articles made of or coated with such materials as collagen; regenerated collagen; polylactic acid; hyaluronic acid; biocompatible metals such as stainless steel and titanium; ceramic materials including prosthetic materials such as hydroxylapatite; synthetic polymers, including polyesters and nylons; biological materials that are actually part of a patient, such as connective tissue and other organs, and virtually any other material to which biological molecules can readily adhere.

Fetal pancreatic islet cells may be grown in vitro in the presence of laminin 5 for transplantation into diabetic patients. Growth of fetal pancreatic islet cells in the presence of laminin 5 increases the yield of islet cells for transplantation and thus solves the long felt but unsolved need of producing larger amounts of these cells. Since the matrix secreted by the NBT-II rat bladder carcinoma cell line contains the same protein components found in the matrix secreted by 804G cells, its use as a substrate for the growth of pancreatic islet cells is advantageously envisioned, as is any such "804G" matrix protein, including all such proteins secreted by cell lines which are capable of enhancing the growth of pancreatic islet cells. In addition, it is contemplated that the inclusion of growth factor in the adult islet cell culture medium will further increase the yield of islet cells.

The resulting islet cells are fully functional after transplantation into mammals, preferably humans, and will reduce or eliminate the need for insulin injections. It is envisioned that after routine optimization of the growth conditions, an even greater increase in the number of ICCs can be obtained.

The 804G matrix of the present invention comprises three concanavalin-binding glycosylated proteins, of approximately 135 kD, 140 kD and 150 kD, all of which are recognized by polyclonal antibodies raised against the 804G matrix. The methods of the present invention may be practiced with the complete, active matrix from 804G cells or a functionally equivalent "804G" matrix from other cells, and may also be practiced with any one of the individual protein components of the matrix which promote enhanced islet cell growth. The same statement applies to the individual protein components of any of the other laminin 5 molecules described herein. Cell matrix and matrix proteins can be readily screened for the ability to enhance growth of pancreatic islet cells, using the techniques described herein. Only routine experimentation is required.

In addition to the active molecules and the active components thereof, the present invention also includes shaped articles coated with those materials. Preferably, those shaped articles are formed of materials other than glass, and include such forms as sheets, fabrics, prostheses, metal articles, bioerodible articles, and implantable articles.

The extracellular matrix may be harvested (as by scraping, abrading, or treatment with low concentrations of SDS) from surfaces on which appropriate matrix-depositing cells have been grown (See U.S. Pat. No. 5,541,106). Alternatively, the matrix materials may be prepared synthetically or through recombinant DNA techniques using, for example, murine or human cDNA libraries, or through purification of deposited matrix material. The extracellular matrix may also be isolated in soluble form by harvesting the conditioned medium from 804G, NBT-II, MCF 10A or human keratinocytes which is may be used to coat substrates on which the islet cells are cultured. Moreover, the particular molecule of interest may be purified and used to coat the substrate. The extracellular matrix deposited by the cell lines may also be used after removal of the cells, without further processing or purification. In this embodiment, islet cells are cultured on the matrix directly after removal of 804G or NBT-II cells from the matrix.

Soluble and insoluble laminin 5 is isolated from MCF 10A cells as described in the following example.

EXAMPLE 1

Isolation of laminin 5 from MCF 10A cells

The insoluble matrix was prepared from five day old MCF 10A cultures as described for 804G cells in U.S. Pat. No. 5,541,106. Briefly, cell monolayers were washed in phosphate buffered saline (PBS), then treated for about five minutes with 20 mM $NH_4OH$. Cell remnants were washed from the substrate with PBS.

EXAMPLE 2

Expansion of fetal pancreatic islet cells in vitro

Human fetal pancreas is minced into 1 mm pieces in cold Hanks' balanced salt solution (HBSS) and digested with collagenase P by shaking vigorously for 15 min in a water bath at 37° C. After several washes at 4° C. with HBSS, the digested tissue is washed with cold HBSS and placed into petri dishes in RPMI-1640 medium containing 10% pooled human serum and antibiotics for three days. Optionally, a growth factor is present during this procedure.

Approximately 50 ICCs of uniform size (50–75 μm diameter) and homogeneous translucent appearance are hand picked and plated on tissue culture dishes coated with either 804G matrix, kalinin, epiligrin, MCF 10A matrix, bovine corneal matrix or no matrix in RPMI-1640 containing 15% horse serum, 5% FCS, antibiotics and, optionally, a growth factor. ICCs attach overnight and monolayer formation is generally initiated by 24 hours. A significant increase is observed in the number of ICCs plated on any of the laminin 5 matrices compared to either no matrix or to bovine corneal matrix.

To determine whether these fetal endocrine cells are capable of differentiating into insulin-producing cells in vivo, ICCs are transplanted as described below.

EXAMPLE 3

Transplantation of ICCs into nude mice

ICCs obtained according to Example 2 are transplanted under the kidney capsule of athymic nude mice (approximately 500 ICCs per mouse) and the grafts are analyzed after 3 months. An increased level of human C-peptide, released into the blood after processing of the insulin precursor molecule, is detected in the blood of grafted animals by radioimmunoassay after an intraperitoneal glucose challenge indicating that the grafted cells are able to produce insulin. In addition, immunocytochemistry of graft cells using an antibody to insulin indicates that the precursor cells differentiate into insulin-producing cells.

EXAMPLE 4

Transplantation of ICCs into diabetic patients

Human diabetes patients are administered a number of fetal ICCs to be optimized in clinical studies. Presumably, this number will be close to that used for adult-derived cells, approximately $2-8\times10^5$, either by implantation under the kidney capsule or by direct injection into the liver. In addition, transplantation in other ectopic organ locations is also contemplated. C-peptide production and blood glucose levels are monitored over several months to determine whether transplanted ICCs have differentiated into insulin-producing cells. The patients are still administered insulin during the monitoring period.

EXAMPLE 5

Glucose responsiveness of expanded islet cells

Glucose responsiveness of the islet cells expanded as described in Example 2 is determined per unit DNA in response to a glucose/theophylline static challenge. Cells are incubated in a low glucose medium (100 mg/dl–RPMI+2% serum) for at least three days prior to a glucose challenge. The cells are then incubated for 30 minutes in either a resting concentration of glucose (50 mg/dl) or stimulated with 325 mg/dl glucose plus 10 mM theophylline. Cells are collected from the dish, sonicated and processed as described below.

The results indicate that the expanded ICCs respond to a glucose challenge by secreting insulin into the cell culture supernatant and upon removal of the stimulation, revert to a lower insulin secretion level.

EXAMPLE 6

Determination of insulin content

Insulin content is determined and expressed as a ratio of cellular insulin/DNA. After glucose responsiveness determination, plated cells are washed once with PBS and then with 1 ml water per well was added. The wells containing the attached cells are frozen at −20° C. Plates are thawed and cells are removed by mechanical scraping. For islet-like cell clusters or reaggregated cells, the concentration is 100 ICCs/ml. The cells are sonicated at setting number 3 on a Fisher Scientific 60 Dismembrator for 10 seconds or until no particulate matter is observed by gross visual inspection. The samples are then stored at −20° C. until performing an insulin ELISA using a kit from Peninsula Laboratories, Belmont, Calif.

DNA content is determined using a fluorometric dye (Hoechst 33258, American Hoechst Co.). A working solution of the dye is prepared immediately before use by diluting a 1.0 mg/ml stock solution of dye 2000 fold in dye dilution buffer (10 mM Tris HCl, pH 7.4, 1 mM EDTA, 0.1 mM NaCl) to yield a dye concentration of 0.5 μg/ml. A standard solution of calf thymus DNA (100 μg/ml) is prepared and diluted to obtain standard solutions ranging from 0 μg/ml to 15 μg/ml. The assay is formatted to individual fluorometer cuvettes per sample. A Turner Model 450 fluorometer is set at an excitation wavelength to 360 nm, an emission wavelength of 450 nm, and a 7 mm light aperture. Two ml dye solution is added to each cuvette followed by addition of 250 μl of standard or sample solution. The samples are incubated at room temperature for 30–45 min in the dark, and then read on a fluorometer at 360 nm and 450 nm. The DNA content in the samples is determined by fitting the fluorescent unit value obtained for each sample against the standard curve slope of fluorescent units versus concentration.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of growing cells of pancreatic islet-like cell clusters (ICCs), comprising the step of culturing said ICCs in culture media in contact with laminin 5, with the proviso that said laminin 5 is not rat laminin 5.

2. The method of claim 1, wherein said ICCs are from a mammal.

3. The method of claim 2, wherein said ICCs are from a human.

4. The method of claim 1, wherein said laminin 5 is selected from the group consisting of kalinin and epiligrin.

5. The method of claim 1, wherein said laminin 5 is the extracellular matrix obtainable from MCF 10A cells, ATCC CRL-10317.

6. The method of claim 1, wherein said laminin 5 is of human origin.

7. The method of claim 1, wherein said ICCs are expanded at least 5 fold and the expanded ICCs secrete insulin.

8. The pancreatic ICCs prepared in accordance with claim 1.

9. A method of treating Type I diabetes in a patient in need thereof, comprising the step of administering to said patient an effective insulin-producing amount of the ICCs of claim 8.

10. The method of claim 9, wherein said administering step is by implantation under the kidney capsule.

11. The method of claim 10, wherein said ICCs are placed in an immunoprotective barrier prior to said implantation.

12. The method of claim 9, wherein said administering step is by direct injection into the liver.

13. The method of claim 9, wherein said effective insulin-producing amount is between about $2 \times 10^5$ and about $8 \times 10^5$ ICCs.

* * * * *